(12) United States Patent
Viole et al.

(10) Patent No.: US 7,491,163 B2
(45) Date of Patent: Feb. 17, 2009

(54) MULTILUMEN CATHETER FOR MINIMIZING LIMB ISCHEMIA

(75) Inventors: Anthony Viole, Foothill Ranch, CA (US); Laksen Sirimanne, Irvine, CA (US); Steven F. Bolling, Ann Arbor, MI (US); Shawn O'Leary, Mission Viejo, CA (US); Robert Pecor, Aliso Viejo, CA (US); Ryan Kelly, San Diego, CA (US); Wolfgang Werner, Carlsbad, CA (US); Masoud Beizai, Laguna Hills, CA (US)

(73) Assignee: Orqis Medical Corporation, Lake Forest, CA (US)

( * ) Notice: Subject to any disclaimer, the term of this patent is extended or adjusted under 35 U.S.C. 154(b) by 206 days.

(21) Appl. No.: 11/417,647

(22) Filed: May 3, 2006

(65) Prior Publication Data

US 2006/0264689 A1 Nov. 23, 2006

Related U.S. Application Data

(60) Division of application No. 10/078,283, filed on Feb. 14, 2002, which is a continuation-in-part of application No. 09/876,281, filed on Jun. 6, 2001, now Pat. No. 7,048,680.

(51) Int. Cl.
*A61N 1/362* (2006.01)
*A61M 1/00* (2006.01)
*A61M 3/00* (2006.01)

(52) U.S. Cl. .................. 600/16; 604/28; 604/43
(58) Field of Classification Search .......... 600/16–18; 604/4.01, 6.11, 43, 28; 623/3.1
See application file for complete search history.

(56) References Cited

U.S. PATENT DOCUMENTS 1,902,418 A 3/1933 Pilgrim (Continued)

FOREIGN PATENT DOCUMENTS

EP 0405749 1/1991

(Continued)

OTHER PUBLICATIONS

PCT International Search Report dated Jun. 7, 205; PCT/US2004/037636, 13 pp.

(Continued)

*Primary Examiner*—Mark W Bockelman
(74) *Attorney, Agent, or Firm*—Knobbe, Martens, Olson & Bear, LLP.

(57) ABSTRACT

A multilumen catheter that maximizes the blood flow into and out of the patient's vasculature while also providing for passive and/or active perfusion of tissue downstream of where the catheter resides in the vasculature. The inventive catheter comprises a proximal end, a first distal and a second distal end with first and second lumens extending from the proximal end to each of these distal ends to provide for blood circulation within one blood vessel or between two different blood vessels. The second lumen, and any additional lumens so desired, may be positioned coaxially with or radially around the first lumen. Redirecting means is provided at a distal end of at least one of said lumens for directing blood in a direction generally opposite of the direction of flow through said lumen.

19 Claims, 8 Drawing Sheets

U.S. PATENT DOCUMENTS

| | | |
|---|---|---|
| 2,876,769 A | 3/1959 | Cordova |
| 2,935,068 A | 5/1960 | Donaldson |
| 3,017,885 A | 1/1962 | Robicsek |
| 3,410,263 A | 11/1968 | McGinnis |
| 3,938,530 A | 2/1976 | Santomieri |
| 4,080,958 A | 3/1978 | Bregman et al. |
| 4,134,402 A | 1/1979 | Marhurkar |
| 4,149,535 A | 4/1979 | Volder |
| 4,375,941 A | 3/1983 | Child |
| 4,405,313 A | 9/1983 | Sisley et al. |
| 4,459,977 A | 7/1984 | Pizon et al. |
| 4,464,164 A | 8/1984 | Troutner et al. |
| 4,540,402 A | 9/1985 | Aigner |
| 4,543,087 A | 9/1985 | Sommercorn et al. |
| 4,692,141 A | 9/1987 | Mahurkar |
| 4,897,077 A | 1/1990 | Cicciu et al. |
| 4,902,272 A | 2/1990 | Milder et al. |
| 4,944,745 A | 7/1990 | Sogard et al. |
| 4,957,504 A | 9/1990 | Chardack et al. |
| 4,960,411 A | 10/1990 | Buchbinder et al. |
| 4,976,270 A | 12/1990 | Parl et al. |
| 4,985,014 A | 1/1991 | Orejola |
| 4,995,857 A | 2/1991 | Arnold |
| 5,014,715 A | 5/1991 | Chapolini |
| 5,059,167 A | 10/1991 | Lundquist et al. |
| 5,087,247 A | 2/1992 | Horn et al. |
| 5,129,883 A | 7/1992 | Black |
| 5,147,281 A | 9/1992 | Thornton et al. |
| 5,186,713 A | 2/1993 | Raible |
| 5,318,518 A | 6/1994 | Plechinger et al. |
| 5,374,245 A | 12/1994 | Mahurkar |
| 5,378,230 A | 1/1995 | Mahurkar |
| 5,403,291 A | 4/1995 | Abrahamson |
| 5,437,601 A | 8/1995 | Runge |
| 5,472,417 A | 12/1995 | Martin et al. |
| 5,486,159 A | 1/1996 | Mahurkar |
| 5,522,800 A | 6/1996 | Crocker |
| 5,533,957 A | 7/1996 | Aldea |
| 5,536,250 A | 7/1996 | Klein et al. |
| 5,542,937 A | 8/1996 | Chee et al. |
| 5,554,136 A | 9/1996 | Luther |
| 5,556,390 A | 9/1996 | Hicks |
| 5,571,093 A | 11/1996 | Cruz et al. |
| 5,616,137 A | 4/1997 | Lindsay et al. |
| 5,618,267 A | 4/1997 | Palestrant |
| 5,722,930 A | 3/1998 | Larson et al. |
| 5,746,709 A | 5/1998 | Rom et al. |
| 5,766,151 A | 6/1998 | Valley et al. |
| 5,776,111 A | 7/1998 | Tesio |
| 5,776,151 A | 7/1998 | Chan |
| 5,785,686 A | 7/1998 | Runge |
| 5,795,326 A | 8/1998 | Siman |
| 5,807,311 A | 9/1998 | Palestrant |
| 5,868,703 A | 2/1999 | Bertolero et al. |
| 5,928,181 A | 7/1999 | Coleman et al. |
| 5,947,953 A | 9/1999 | Ash et al. |
| 5,961,486 A | 10/1999 | Twardowski et al. |
| 5,965,089 A | 10/1999 | Jarvik et al. |
| 6,044,845 A | 4/2000 | Lewis |
| 6,053,900 A | 4/2000 | Brown et al. |
| 6,059,760 A | 5/2000 | Sandmore et al. |
| 6,083,198 A | 7/2000 | Afzal |
| 6,135,981 A | 10/2000 | Dyke |
| 6,167,765 B1 | 1/2001 | Weitzel |
| 6,200,260 B1 | 3/2001 | Bolling |
| 6,245,045 B1 | 6/2001 | Stratienko |
| 6,287,608 B1 | 9/2001 | Levin et al. |
| 6,293,958 B1 | 9/2001 | Berry et al. |
| 6,299,575 B1 | 10/2001 | Bolling |
| 6,371,935 B1 | 4/2002 | Macoviak et al. |
| 6,387,037 B1 | 5/2002 | Bolling et al. |
| 6,390,969 B1 | 5/2002 | Bolling et al. |
| 6,428,464 B1 | 8/2002 | Bolling |
| 6,488,662 B2 | 12/2002 | Sirimanne |
| 6,508,777 B1 | 1/2003 | Macoviak et al. |
| 6,514,226 B1 | 2/2003 | Levin et al. |
| 6,558,356 B2 | 5/2003 | Barbut |
| 6,592,567 B1 | 7/2003 | Levin et al. |
| 6,610,004 B2 | 8/2003 | Viole et al. |
| 6,685,621 B2 | 2/2004 | Bolling et al. |
| 6,719,749 B1 | 4/2004 | Schweikert et al. |
| 6,889,082 B2 | 5/2005 | Bolling et al. |
| 7,048,680 B2 | 5/2006 | Viole et al. |
| 7,125,376 B2 | 10/2006 | Viole et al. |
| 2002/0111577 A1 | 8/2002 | Sirimanne et al. |
| 2002/0169413 A1 | 11/2002 | Keren et al |
| 2002/0188167 A1 | 12/2002 | Viole et al. |
| 2003/0040736 A1 | 2/2003 | Stevens et al. |
| 2003/0083617 A1 | 5/2003 | St. Germain et al. |
| 2003/0144628 A1 | 7/2003 | Sirimanne |
| 2004/0116768 A1 | 6/2004 | Bolling et al. |
| 2004/0138519 A1 | 7/2004 | Viole et al. |
| 2004/0236172 A1 | 11/2004 | Bolling et al. |
| 2005/0085683 A1 | 4/2005 | Bolling et al. |
| 2005/0113631 A1 | 5/2005 | Bolling et al. |
| 2005/0256363 A1 | 11/2005 | Bolling et al. |
| 2005/0277803 A1 | 12/2005 | Pecor |
| 2005/0277804 A1 | 12/2005 | Pecor |
| 2005/0277870 A1 | 12/2005 | Pecor |
| 2006/0264693 A1 | 11/2006 | Viole et al. |
| 2006/0264694 A1 | 11/2006 | Viole et al. |
| 2006/0264797 A1 | 11/2006 | Viole et al. |
| 2006/0264798 A1 | 11/2006 | Viole et al. |
| 2006/0264800 A1 | 11/2006 | Bolling et al. |
| 2006/0264801 A1 | 11/2006 | Bolling et al. |
| 2006/0270890 A1 | 11/2006 | Viole et al. |
| 2006/0270891 A1 | 11/2006 | Viole et al. |
| 2006/0270892 A1 | 11/2006 | Bolling et al. |
| 2006/0270893 A1 | 11/2006 | Bolling et al. |
| 2006/0270895 A1 | 11/2006 | Viole et al. |
| 2006/0270963 A1 | 11/2006 | Bolling et al. |
| 2006/0270964 A1 | 11/2006 | Viole et al. |
| 2006/0270965 A1 | 11/2006 | Viole et al. |
| 2006/0270966 A1 | 11/2006 | Bolling et al. |
| 2006/0276681 A1 | 12/2006 | Bolling |
| 2006/0276682 A1 | 12/2006 | Bolling et al. |
| 2006/0281962 A1 | 12/2006 | Bolling et al. |

FOREIGN PATENT DOCUMENTS

| | | |
|---|---|---|
| EP | 0411605 | 2/1991 |
| EP | 0 533 432 A1 | 3/1993 |
| EP | 0 711 574 A1 | 5/1996 |
| EP | 0 836 861 | 4/1998 |
| EP | 1 407 798 | 4/2004 |
| FR | 2 201 908 | 5/1974 |
| GB | 1 370 546 | 10/1974 |
| GB | 2174151 | 10/1986 |
| JP | S58-190448 | 5/1985 |
| JP | 08257001 | 10/1996 |
| WO | WO 96/17644 | 6/1996 |
| WO | WO 98/14225 | 4/1998 |
| WO | WO 98/28034 | 7/1998 |
| WO | WO 99/07301 | 2/1999 |
| WO | WO 99/19010 | 4/1999 |
| WO | WO 99/42156 | 8/1999 |
| WO | WO 99/59652 | 11/1999 |
| WO | WO 99/65546 | 12/1999 |
| WO | WO 00/04943 | 2/2000 |
| WO | WO 00/12148 | 3/2000 |
| WO | WO 00/38591 | 7/2000 |
| WO | WO 00/61207 | 10/2000 |
| WO | WO 02/064204 | 8/2002 |

| | | |
|---|---|---|
| WO | WO 03/068303 | 8/2003 |

OTHER PUBLICATIONS

PCT International Search Report dated Jun. 27, 2000, App. No. PCT/US 00/06749, 4 pp.

PCT International Search Report dated Aug. 6, 2002, App. No. PCT/US 01/42774, 6 pp.

PCT International Search Report dated Jun. 18, 2003, App. No. PCT/US 03/04401, 4 pp.

PCT International Preliminary Examination Report dated Sep. 29, 2003, App. No. PCT/US 01/42774.

PCT International Search Report dated Nov. 10, 2003; App. No. PCT/US 03/04401, 9 pp.

European Patent Office Office Action dated Apr. 11, 2005; European Application No. 01 983 207.0-2310.

MULTILUMEN CATHETER FOR MINIMIZING LIMB ISCHEMIA

RELATED APPLICATIONS

This application is a divisional of U.S. application Ser. No. 10/078,283, filed Feb. 14, 2002, which is a continuation-in-part of U.S. application Ser. No. 09/876,281, filed Jun. 6, 2001, now U.S. Pat. No. 7,048,680, both of which are incorporated herein in their entireties by reference.

BACKGROUND OF THE INVENTION

1. Field of the Invention

The present invention relates to a multilumen catheter and, in particular, to multilumen catheters designed to prevent ischemia in patients when the catheter is positioned within the body.

2. Description of the Related Art

It is often necessary to divert the flow of blood from a patient's blood vessel back to the same or a different blood vessel as part of treating a patient suffering from one or more of numerous health impairments, including cardiovascular disease, such as congestive heart failure. Although surgical cut-down procedures can achieve this, percutaneous insertion of catheters has made this procedure less invasive and therefore less traumatic to the patient. Still, insertion of a cannula into the circulatory system can cause complex, and sometimes adverse, reactions within the body.

Some of the percutaneous procedures involve removing blood from the body and subsequently returning it to the body. For example, dialysis treatment involves first removing blood from the patient's circulatory system, treating the blood outside of the body, and then returning the blood to the patient's circulatory system to perfuse the various tissues and organs. Depending on the volume of blood flow, cannulae with large carrying capacity may be necessary. By maximizing the cross-sectional area of the cannula, the volume of blood that may be removed and/or returned to the patient's vascular system via the cannula is maximized. One approach to maximize the cross-sectional area of the cannula involves using either two single lumen catheters or a multi-lumen catheter. In a recirculation application, one lumen would function to withdraw blood and one would function to return blood to the patient. One problem with using two single lumen catheters is that it subjects the patient to multiple percutaneous insertion procedures, which complicates the procedure and increases the potential for infection and other complications. Therefore, it would be desirable to have a catheter assembly which could be inserted into the patient through a single insertion site.

Multilumen catheters in various forms have been employed for this purpose. For example, multilumen catheters have been made with two, three or more lumens to serve various aspiration and infusion functions, including extracting and returning blood to vessels, taking blood samples for testing and providing medications to the patient's vascular system. Simple multilumen catheters have been made by providing two round catheters of equal or nearly equal length joined by a web, or thin strip. This approach is described in U.S. Pat. No. 5,776,111 to Tesio. Other multilumen catheter designs have a unitary body with at least one septum dividing the lumens which extend from a proximal to a distal end.

While multilumen catheters require only a single puncture of the epidermis, their performance is limited in at least two ways. For one, the outer perimeter of the multilumen catheter cannot exceed the inner diameter of the vessel into which it is inserted. Furthermore, the already limited cross-sectional area must be divided into at least two lumens, one for withdrawal and one for return. Thus the carrying capacity of each lumen is further reduced. To supply the same amount of blood, the velocity and pressure of the blood in the lumens must increase over what it would be in the vessel itself. This has the potential to cause damage to the vessel as blood comes jetting out of the return lumen. Also, it may put further stress upon blood cells, even causing hemolysis. Thus, multilumen catheters must be made as large as possible to carry enough blood at satisfactory conditions.

Where the size of a catheter approaches the interior size of a vessel, less and less blood can flow around the catheter. As a result, limited blood supply reaches tissues and organs located downstream of the catheter in the vascular system. With insufficient perfusion, the tissues downstream of the lumen insertion site suffer from ischemia and become oxygen deprived. Prolonged oxygen deprivation can lead to tissue damage, as is well known in the art. Therefore, it would be desirable to have a multilumen catheter that can maximize cross-sectional area of withdrawal and return lumens while at the same time providing for acceptable levels of blood perfusion of tissue downstream of the catheter insertion site in the vascular system. It would also be advantageous to have a multilumen catheter that can also remove blood from one peripheral vessel and return blood to a second peripheral vessel.

SUMMARY OF THE INVENTION

Overcoming many if not all of the limitations of the prior art, the present invention comprises a multilumen catheter for directing the flow of blood to and from a patient through a single cannulation site. The catheter comprises a proximal end, a first distal end and a second distal end. The first distal end extends farther from the proximal end than the second distal end. A first lumen extends between the first distal end and the proximal end and a second lumen extends between the second distal end and the proximal end. At least one aperture, but preferably a plurality of apertures may be formed in one of the first or second lumens positioned near the proximal end so that the aperture permits active maintenance or enhancement of perfusion of blood to the patient's vasculature downstream of where the aperture resides in the vasculature when the catheter is inserted into the patient for treatment.

In an alternative embodiment, the multilumen catheter further comprises a third lumen with distal and proximal ends configured to be positioned entirely within the patient's vascular system. This third lumen is configured to permit the passive flow of blood downstream of the catheter site to maintain or enhance perfusion.

In another embodiment, the multilumen catheter also comprises means for redirecting at least a portion of the blood flow exiting a lumen of the catheter in a direction generally opposite of the direction of flow of blood in the catheter. In one embodiment, the redirecting means is a redirecting tip positioned at the distal end of one of the lumens. In this embodiment, the redirecting tip is configured to redirect at least a portion of the blood flow exiting the lumen in a direction generally opposite of the direction of flow.

In one embodiment, a connector formed in the shape of a Y ("Y-connector") is positioned at the proximal end of the multilumen catheter. One leg of the Y-connector is in fluid communication with the first lumen and the other leg of the Y-connector is in fluid communication with the second lumen.

Preferably, in an application of the present invention, an outflow conduit of a pumping system is fluidly engaged to one lumen of the multilumen catheter and an inflow conduit of the same system is fluidly engaged to the other lumen. The inflow and outflow conduits are fluidly coupled to a pump so that, when connected to the patient, the pump circulates blood from one distal end of the multilumen catheter to the other distal end, and also through at least one aperture in one of the first or second lumens positioned near the proximal end. In one application, the multilumen catheter of the present invention is incorporated into an extracardiac pumping system for supplementing blood circulation in a patient without any component thereof being connected to the patient's heart. Such a system is described in U.S. Pat. Nos. 6,200,260 and 6,299,575, which are incorporated herein by reference. The system includes, in addition to the multilumen catheter, a pump configured to pump blood through the patient at subcardiac rates, an inflow conduit fluidly coupled to the pump to divert blood to the pump from a first blood vessel, and an outflow conduit fluidly coupled to the pump to direct blood from the pump to a second blood vessel.

Another embodiment of the present invention is an extracardiac pumping system for supplementing blood circulation through a patient without any component thereof being connected to the patient's heart. The extracardiac system comprises a multilumen catheter that has at least two lumens therethrough. Each lumen has a distal end configured for insertion into the patient's vasculature and a proximal end. At least two of the lumens are in fluid communication with each other at their proximal end. The extracardiac pumping system also comprises a pump secured within one of the lumens and configured to pump blood through the patient at subcardiac volumetric rates. The pump has an average flow rate that, during normal operation thereof, is substantially below that of the patient's heart when healthy. The pump can be operated to pump blood from one location in the patient's vasculature to a different location in the vasculature while the proximal end of each lumen resides outside the patient's body.

The present invention also provides a method for treating a patient using one of the multilumen catheters of the present invention. The method comprises the step of inserting the multilumen catheter described above into the patient at a single cannulation site of a first blood vessel, locating the catheter such that a first lumen may be in fluid communication with a second blood vessel and a second lumen may be in fluid communication with the first blood vessel, withdrawing blood from one of said blood vessels through one of the first or said second lumens, and delivering blood through the other of said first or second lumens so that blood is delivered upstream and downstream of the cannulation site.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENT

Turning now to the drawings provided herein, a more detailed description of the embodiments of the present invention is provided below.

Figure 1:
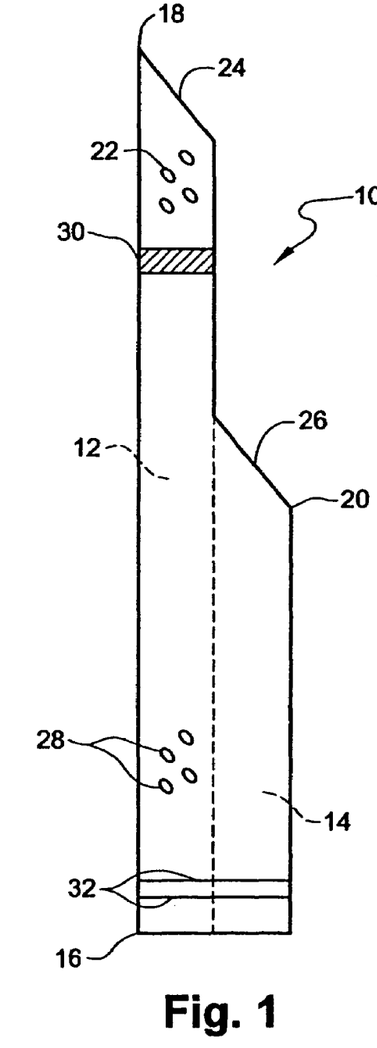
FIG. 1 is a schematic of one embodiment of the present invention multilumen catheter.

With reference to FIG. 1, one embodiment of the present invention comprises a multilumen catheter 10 designed to lessen ischemia that can occur when a large diameter catheter is inserted into a patient's blood vessel. The multilumen catheter preferably is of unitary construction and requires only one entry point into the patient's body. The multilumen catheter 10 comprises at least two lumens: a first lumen 12 and a second lumen 14. The first lumen 12 extends from a proximal end 16 of the multilumen catheter 10 to a first distal end 18. The second lumen 14 extends from the proximal end 16 of the multilumen catheter 10 to a second distal end 20. The lumens 12, 14 of the multilumen catheter 10 may be arranged one of many different ways. For example, the two lumens may be joined in a side-by-side manner, forming a "figure-8" when viewed from the proximal end 16. Alternately, a single cylindrical catheter housing may contain within it two or more side-by-side lumens. A cylindrical catheter housing could be formed with a diametral septum, i.e. a wall, extending across the cylinder at a diameter. A cylindrical housing with concentrically positioned lumens is also contemplated.

The first distal end 18 may be formed with one or more distal apertures 22, although such apertures may also be located in the second distal end 20. The distal apertures 22 may be positioned close together or spaced circumferentially around the distal end. The apertures 22 serve to decrease the pressure drop across the cannula tip, thereby minimizing damage to vessel walls from jetting effects. It may also be appropriate to practice methods for directing blood flow so as to minimize damage to vessel walls from jetting effects and from the recoil effect on the catheter of blood exiting a catheter. The present invention may further comprise a tapered tip 24 at the first distal end 18, which facilitates insertion and threading of the catheter into the patient. The present invention may also further comprise a tapered tip 26 at the second distal end 20.

One preferred embodiment of the multilumen catheter further comprises a set of apertures 28 positioned on the catheter 10 near the proximal end 16. The apertures 28 are formed on at least one lumen of the catheter to provide for fluid communication between one of the lumens 12, or 14 of the multilumen catheter 10 and the blood vessel in which it resides. A radiopaque marker 30 may be positioned at the distal end 18 of the multilumen catheter 10. The multilumen catheter could further comprise markings 32 near the proximal end of the multilumen catheter which are a known distance from one or more of the distal ends. These markings 32, as well as the marker 30 can be used to accurately position the catheter when applied to the patient.

Figure 2:
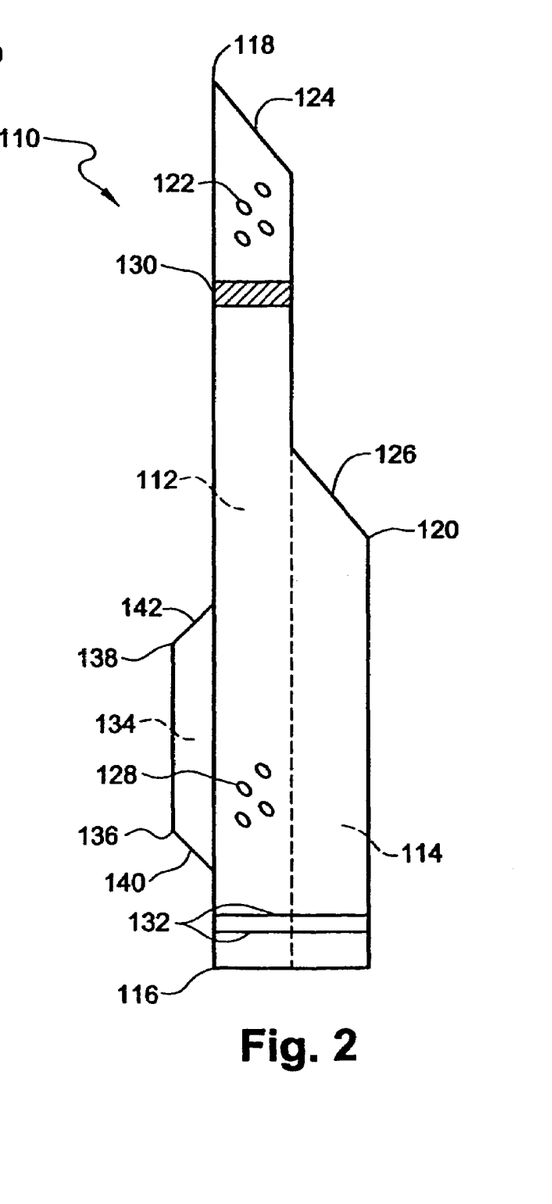
FIG. 2 is a schematic of an alternative embodiment of the present invention multilumen catheter.

In another embodiment of the present multilumen catheter shown in FIG. 2, the multilumen catheter 110 comprises a third lumen 134 extending between a proximal end 136 and a distal end 138. The lumen 134 is positioned and sized such that when the multilumen catheter 110 is applied to the patient (described below), the lumen resides entirely within the patient's body. As described above, the lumen 134 may be connected to the catheter 110 in a variety of ways. The purpose of the third lumen 134 is configured to permit the passive flow of blood downstream to the catheter to enhance perfusion. The embodiment shown in FIG. 2 also may have apertures 128 disposed near the proximal end 116 of the multilumen catheter 110. As described above, this embodiment may further comprise a tapered tip 140 at the distal end of the third lumen 134 and a tapered tip 142 at the proximal end of the third lumen 134 to facilitate application of the catheter to the patient.

In one variation of the three lumen embodiment the third lumen 134 may be made of collapsible material. In the collapsed state, the third lumen 134 would conform to at least a portion of the outside surface of the multilumen catheter 110. Once applied to the patient, as described in more detail below, the lumen 134 would be expanded to the deployed state shown in FIG. 2. This collapsible lumen could comprise a stone basket, or a frame similar to a stent. A stone basket is a structure that can be deployed within a patient's body and is used to capture objects. Here, the basket is used primarily to create a space between the catheter 110 and the vessel wall to permit the passive flow of blood downstream of the catheter site to enhance perfusion.

Figure 3:
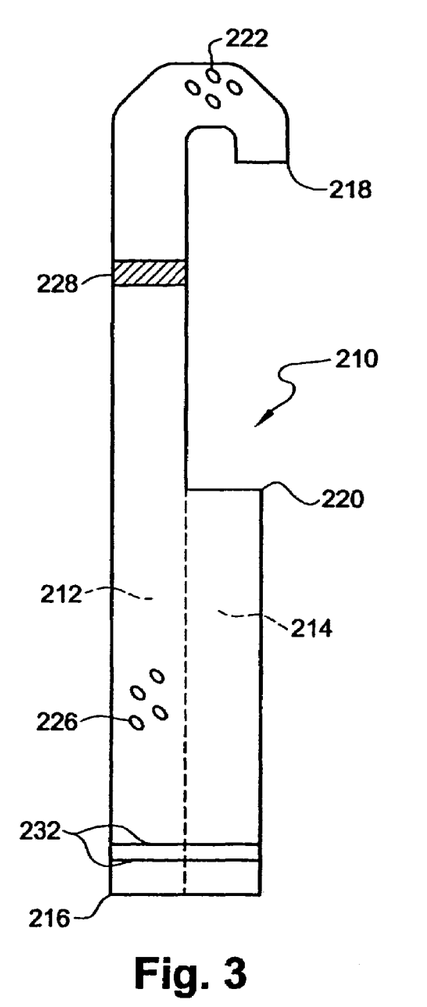
FIG. 3 is a schematic of an alternative embodiment of the present invention multilumen catheter with a distal end comprising a J-tip configuration.

In an alternate embodiment of the multilumen catheter 210, shown in FIG. 3, the first distal end 218 is formed in the shape of a J-tip. That is, the opening at the distal end 218 may be curved such that blood exiting the lumen 212 is directed back along the multilumen catheter 210. Distal aperture(s) 222 may be formed at the bend of the J-tip so that blood also exits the lumen 212 and flows distal of the catheter 210. The "J" shape of the multi-lumen catheter tip may be formed and/or maintained by pre-loading it with a coil or with wire reinforcement, or by using a shape-memory material to create and maintain this shape. If the catheter is inserted so that the tip is straight and the "J" shape is deployed after the catheter inserted into the patient, the catheter may comprise a tapered tip at the first distal end 218, as described above.

Figure 4:
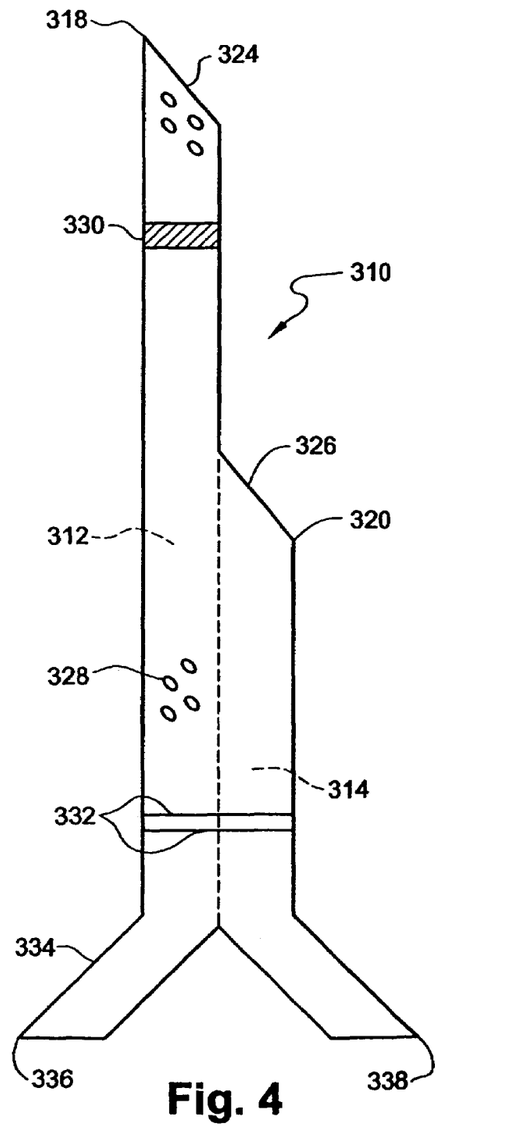
FIG. 4 is a schematic of an alternative embodiment of the present invention multilumen catheter comprising a Y-connector.

Referring to FIG. 4, yet another alternative embodiment of the present invention multilumen catheter 310 comprises a Y-connector 334 formed at the proximal end of the multilumen catheter 310. As described above, the lumens are separated in any suitable way such that fluid communication is provided between the distal end 318 of the lumen 312 of the multilumen catheter 310 and the proximal end 336 of one leg of the Y-connector 334, and fluid communication is provided between the distal end 320 of the lumen 314 of the catheter 310 and the proximal end 338 of one leg of the Y-connector 334.

Any of the multilumen catheters described herein may be made from various materials to improve their viability in long-term treatment applications. For example, it is preferred that the biocompatibility of the catheter be improved compared to uncoated catheters to prevent adverse reactions such as compliment activation and the like. To prevent such side effects, the interior lumens of the catheters can be coated with biocompatible materials. Also known in the art are anti-bacterial coatings. Such coatings may be very useful on the outer surface of the catheter. This is especially true at or about where the catheter enters the patient's skin. At such a location, the patient is vulnerable to introduction of bacteria into the body cavity. Anti-bacterial coatings can reduce the likelihood of infection and thus improve the viability of long-term treatments.

Figure 5:
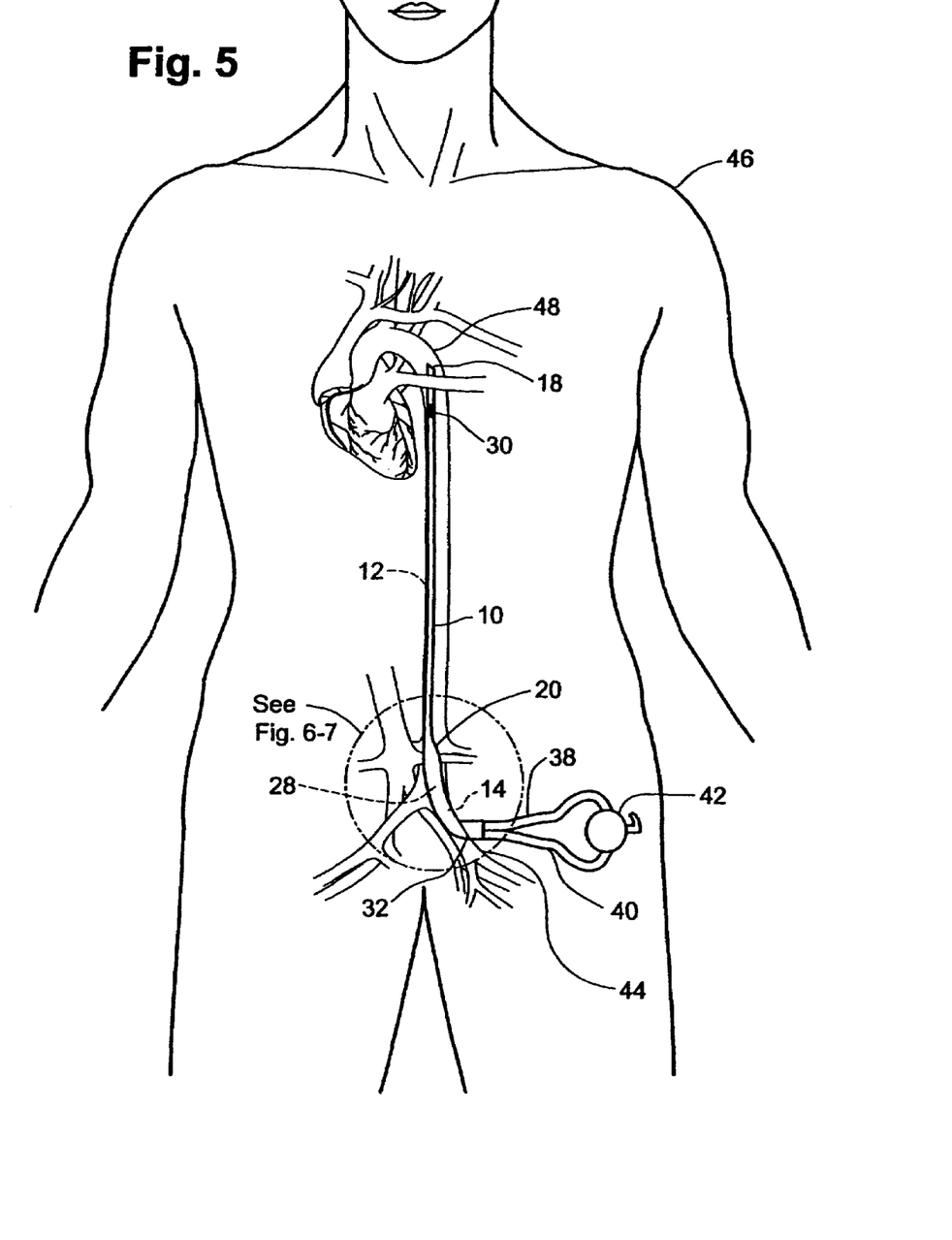
FIG. 5 is a schematic of one application of one embodiment of the multilumen catheter to a patient.

In one application, the multilumen catheter of the present invention may be integrated into a pumping system, such as the one described in more detail in U.S. Pat. No. 6,200,260. Referring to FIG. 5, such a system comprises the multilumen catheter 10, an inflow conduit 38, an outflow conduit 40 and a pump 42. One end of the outflow conduit 40 may be connected to the proximal end of the lumen 12, while the other end is connected to the inlet of the pump 42. One end of the inflow conduit 38 may be connected to the proximal end of the lumen 14, while the other end is connected to the outlet of the pump 42. This results in a flow from the first distal end 18 to the second distal end 20. Of course, the flow direction may be reversed using the same multilumen catheter, resulting in a flow from distal end 20 to distal end 18. In that case, the outflow conduit 40 is connected to the proximal end of lumen 14 and the inflow conduit 38 is connected to the proximal end of lumen 12. Referring to FIG. 5, the present multilumen catheter 10 when incorporated into a pumping system may be applied to a patient in an arterial-arterial fashion. Where the multilumen catheter 10 is inserted into the femoral artery 44 of the patient 46. The radiopaque marker 30 which may be incorporated into the distal end 18 of the multilumen catheter is used to track the insertion of the catheter so that to catheter may be positioned at a desired site within the patient's vascular system. As mentioned above, markings 32 on the proximal end could also be used to locate the distal end or ends.

In one example, the distal end 18 may be located in the aortic arch 48. The pump draws blood from the patient's vascular system in the area near the distal end 18 and into the lumen 12. This blood is further drawn into the lumen of the conduit 40 and into the pump 42. The pump 42 then expels the blood into the lumen of the outflow conduit 38. This lumen carries the blood into the lumen 14 of the multilumen catheter 10 and back into the patient's vascular system in the area near the distal end 20. As described in greater detail below regarding FIGS. 6 and 7, the apertures 28 and/or the third lumen 134 provide blood flow to the patient's vasculature downstream of where the multilumen catheter resides in the vasculature to maintain or enhance perfusion of blood. The blood flow in the multilumen catheter may be reversed. In that case, blood is drawn from the patient through distal end 20 and returned to the patient through distal end 18.

Figure 6:
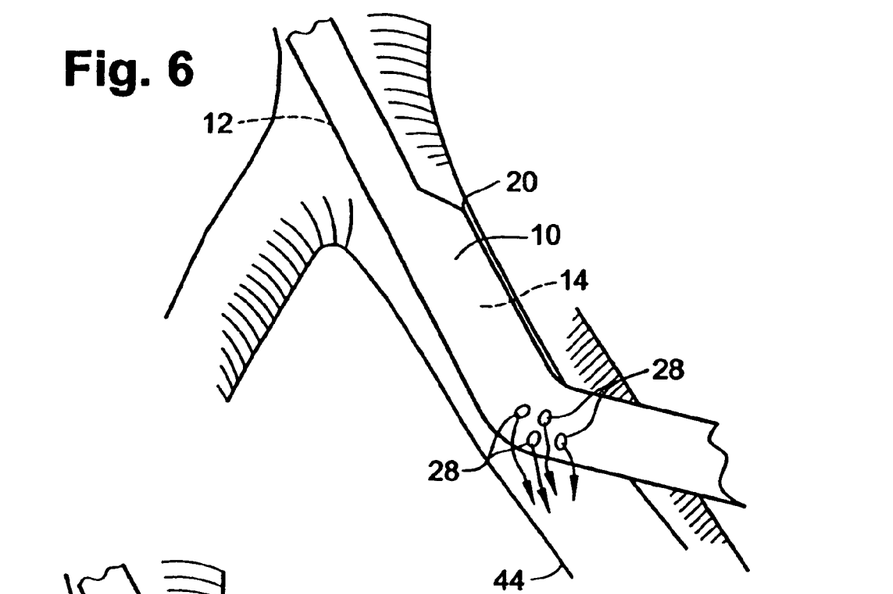
FIG. 6 is an enlarged view of a portion of the proximal end of the embodiment shown in FIG. 1 applied to a patient.

Referring to FIG. 6, the multilumen catheter 10 comprises features that will maintain or increase the blood flow to downstream tissue when the catheter is inserted into the patient. The apertures 28 provide for fluid communication between at least one lumen 12 or 14 and the patient's blood vessel. The apertures 28, thus, provides active perfusion of the downstream tissues.

Figure 7:
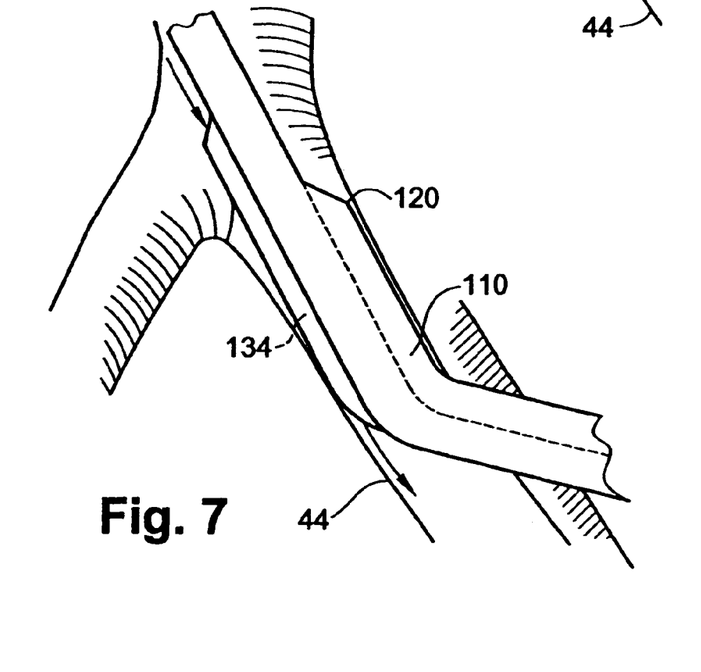
FIG. 7 is an enlarged view of a portion of the proximal end of the embodiment shown in FIG. 2 applied to a patient.

Referring to FIG. 7, the lumen 134 of the embodiment shown in FIG. 2 is located entirely within the vessel when the catheter 110 is inserted into the patient. The lumen provides a pathway for blood flow to tissue downstream of the catheter so that the catheter 110 may maintain or increase the flow of blood to downstream tissue. The lumen 134, thus, provides passive perfusion. If desired, apertures may be included in one of the other two lumens to supplement passive perfusion with active perfusion.

Figure 8:
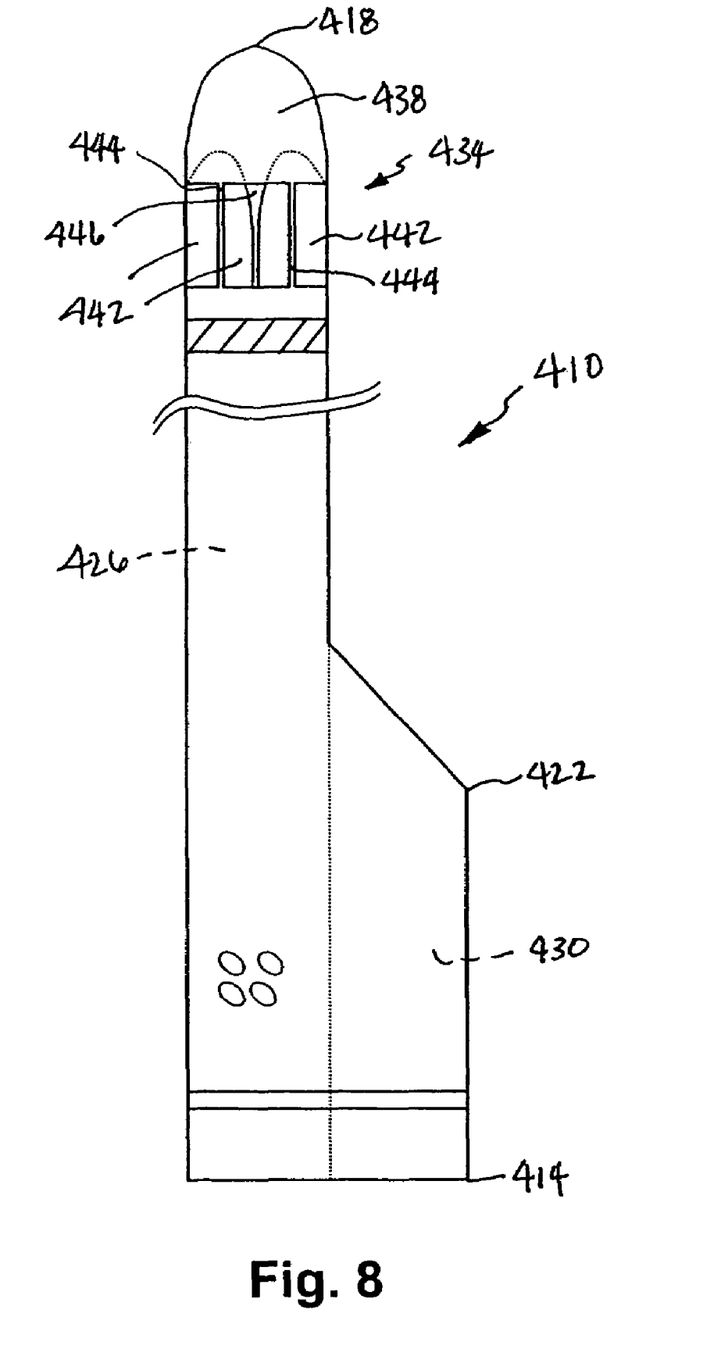
FIG. 8 is a schematic of an alternative embodiment of the present invention multilumen catheter having a redirecting tip.

Referring to FIG. 8, yet another alternative embodiment of the present invention is a multilumen catheter 410 for directing the flow of blood through a patient through a single cannulation site. The catheter 410 comprises a proximal end 414, a first distal end 418, and a second distal end 422. The first distal end 418 extends distally farther from the proximal end 414 than does the second distal end 422. A first lumen 426 extends between the first distal end 418 and the proximal end 414. A second lumen 430 extends between the second distal end 422 and the proximal end 414. As with other embodiments, a radiopaque marker may be provided.

Means for redirecting the flow of blood out of the catheter is provided. For example, in the embodiment of FIG. 8, a redirecting tip 434 is positioned at the distal end of one of the lumens, in this case first lumen 426. The redirecting tip 434 is configured to redirect at least a portion of the blood flow exiting the lumen 426 in a direction generally opposite of the direction of flow of blood in the lumen 426. One of a variety of configurations for a redirecting tip may be employed.

In the embodiment of FIG. 8, the redirecting tip 434 has a closed end 438 at a distal position that is generally hemispherially shaped, although it need not be, and may more particularly have a parabolic profile. Preferably, a plurality of outlets 442 are provided in the side of the lumen 426 that has the redirecting tip 434. These outlets 442 permit blood to flow out of the lumen 426 and into the vasculature of the patient. As shown, the outlets 442 comprise rectangular windows framed by structural elements 444 that connect the closed end 438 to the rest of the catheter 410. It should be recognized that the number and the shape of the outlets 442 can vary.

The redirecting tip 434 further comprises a flow redirecting surface 446 that defines the proximal portion of the closed end 438 and the travel path of the redirected blood. In this embodiment, a cross-section of the flow redirecting surface 446 taken through the longitudinal axis of the lumen 426 reflects two parabolic curves meeting at the longitudinal axis. The three dimensional shape of the redirecting surface 446 of this embodiment is defined by rotating one of the parabolic curves about the longitudinal axis of the lumen 426 in which the surface 446 is positioned. This is one geometrical shape that could be used to form the redirecting surface 446 to gradually redirect the flow of the blood exiting the lumen 426. Other geometrical shapes could be used as well to define the redirecting surface.

The J-tip configuration, discussed above is another means for redirecting blood in a direction generally opposite of the direction of flow of blood through the lumen 426.

Figure 9:
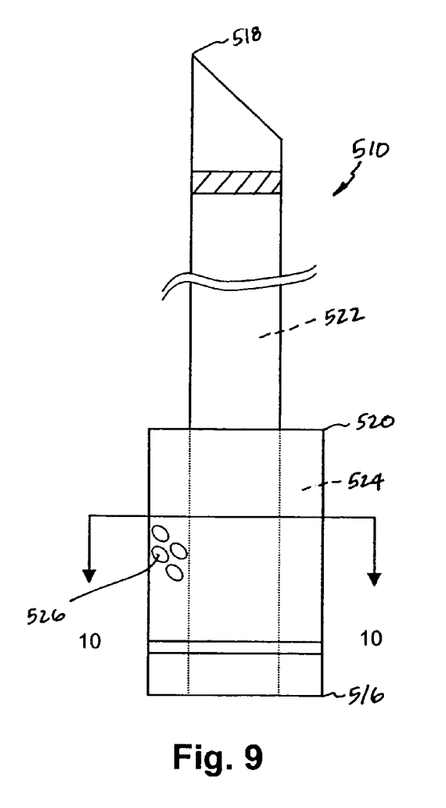
FIG. 9 is a schematic of an alternative embodiment of the present invention multilumen catheter having coaxial lumens.
Figure 10:
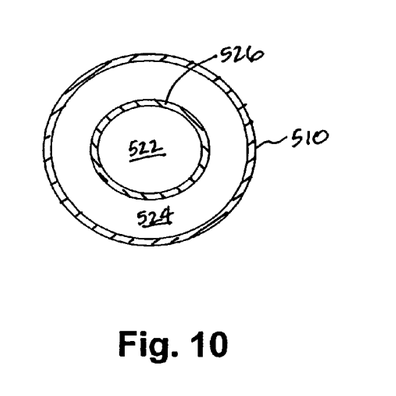
FIG. 10 is a cross-sectional view of the embodiment of FIG. 9.

Referring to FIGS. 9 and 10, a multilumen catheter 510 for directing the flow of blood through a patient through a single cannulation site comprises a proximal end 516 a first distal end 518 and a second distal end 520. The first distal end 518 extends distally farther from the proximal end 516 than the second distal end 520. A first lumen 522 extends between the first distal end 518 and the proximal end 516. A second lumen 524 extends between the second distal end 520 and the proximal end 516, is positioned coaxially with the first lumen 522, and has a diameter greater than the first lumen 522. A radiopaque marker may be provided if desired.

One application of the catheter 510 comprises connecting the second lumen 524 to a patient's blood vessel, preferably via an anastomosis connection after the first lumen 522, which is preferably of tubular configuration, is inserted through the same vessel. In this application, blood may be drawn through the second lumen 524 and redirected into the first lumen 522 using a circulating system such as that disclosed in U.S. Pat. No. 6,200,260. In another application, the first and second lumen may be inserted in the blood vessel in a manner that results in the second lumen 524 extending into the vessel. In this application, if desired, apertures 526 may be provided to permit a more diffuse discharge of blood into the vessel from second lumen 524.

Figure 11:
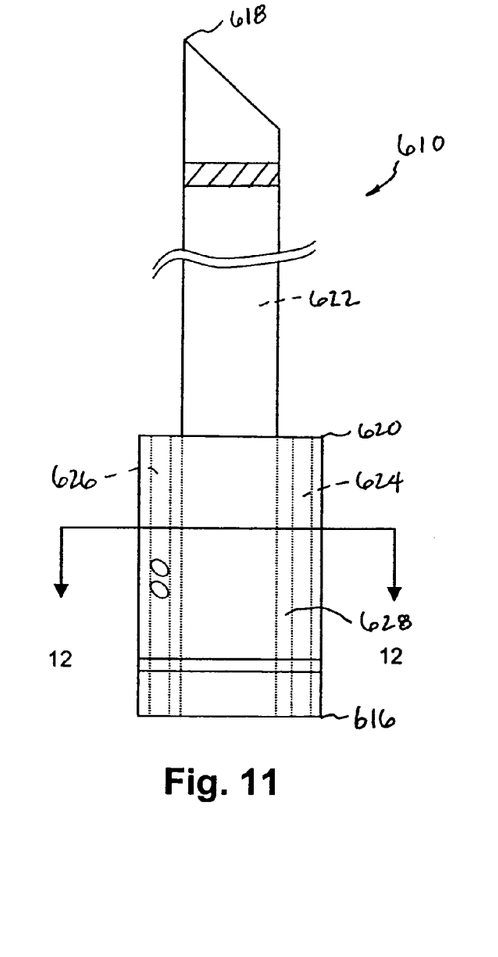
FIG. 11 is a schematic of an alternative embodiment of the present invention multilumen catheter having a second lumen and a third lumen radially housed around a first lumen.
Figure 12:
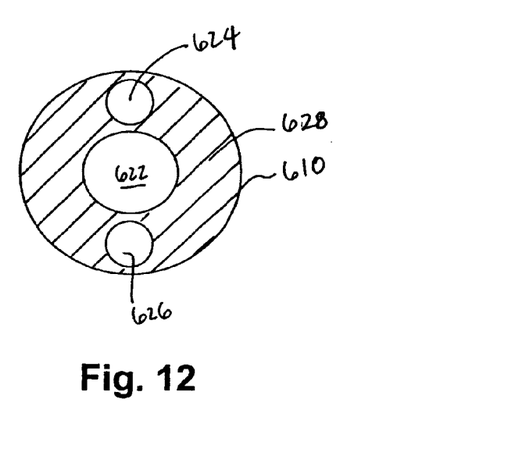
FIG. 12 is a cross-sectional view of the embodiment of FIG. 11.

Referring to FIGS. 11 and 12, a multilumen catheter 610 for directing the flow of blood through a patient through a single cannulation site comprises a proximal end 616, a first distal end 618, and a second distal end 620. The first distal end 618 extends distally farther from the proximal end 616 than the second distal end 620. A first lumen 622 extends between the first distal end 618 and the proximal end 616. A second lumen 624, and if desired a third lumen 626, extend between the second distal end 620 and the proximal end 616. In one application, the third lumen 626 is in fluid communication with the second lumen 624 at a position proximal of the catheter 610, although they need not be. The second lumen 624 and third lumen 626 are positioned radially around the first lumen 622 in a housing 628 that surrounds the first lumen 622, as shown in FIG. 12. One variation of the catheter shown in FIGS. 11 and 12 comprises a fourth lumen in the housing 628 where, if desired, the fourth lumen may be in fluid communication with second lumen 624 and/or third lumen 626 proximal of the catheter. The fourth lumen, as well as the second lumen 624 and the third lumen 626 can be arranged in any suitable manner within the housing 628. In one embodiment, the lumens are arranged symmetrically and radially around the first lumen 622. Asymmetrical arrangements are also contemplated.

Figure 13:
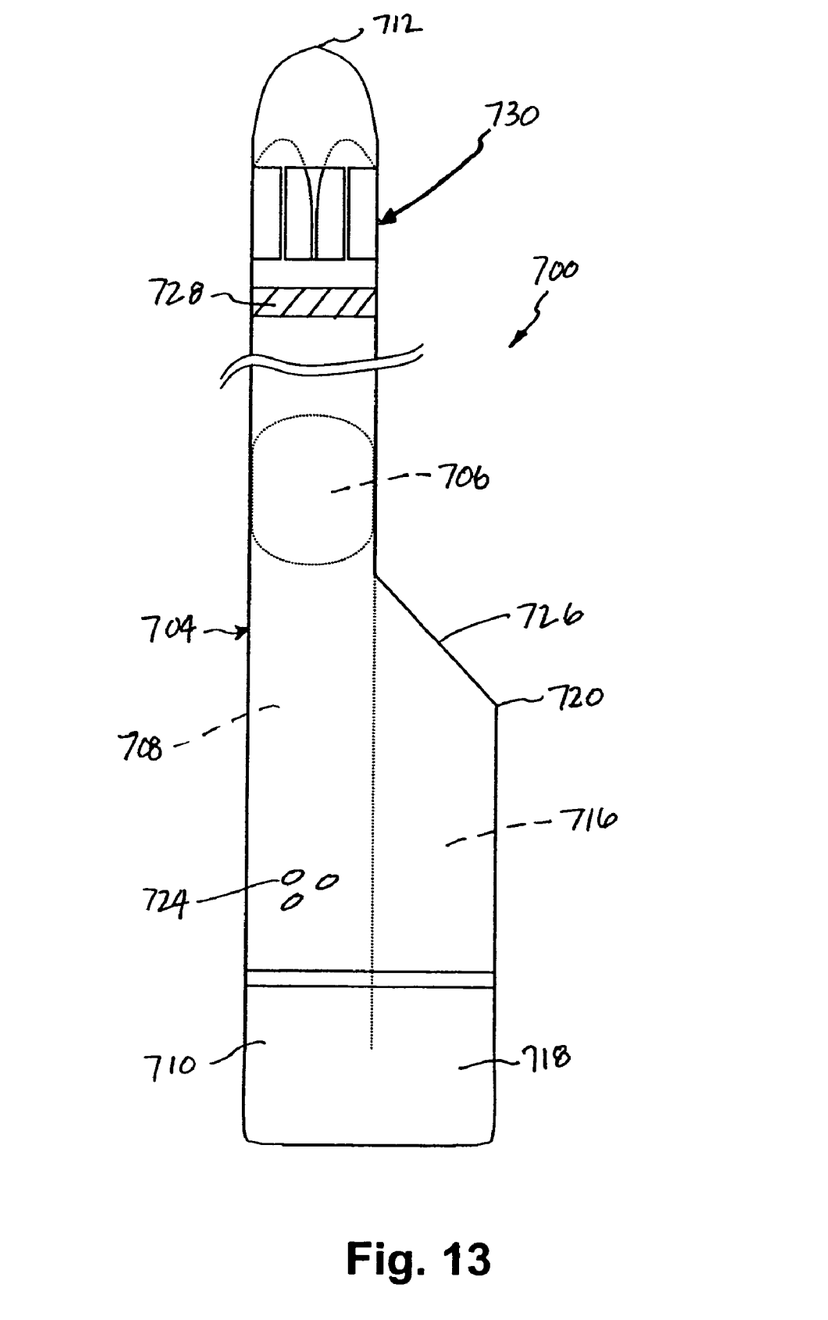
FIG. 13 is a schematic of an extracardiac pumping system for supplementing blood circulation through a patient.

With reference to FIG. 13, another embodiment of the present invention comprises an extracardiac pumping system 700 for supplementing blood circulation through a patient without any component thereof being connected to the patient's heart. The extracardiac system 700 comprises a multilumen catheter 704 and a pump 706 housed within the catheter 704.

The multilumen catheter 704 of the system 700 comprises a first lumen 708 with a proximal end 710 and a distal end 712. The catheter 704 also comprises a second lumen 716 with a proximal end 718 and a distal end 720. In other embodiments, the catheter 704 can have additional lumens, as discussed above. The distal ends 712, 720 are configured for insertion into the patient's vasculature. The two lumens 708, 716 are in fluid communication with each other at their proximal ends 710, 718. First lumen 708 is longer than second lumen 716. In other variations, the lumens 708, 716 could be of the same length.

The pump 706 is secured within one of the lumens 708, 716 and is configured to pump blood through the patient at sub-cardiac volumetric rates the benefits of which are discussed in U.S. Pat. No. 6,200,260. The pump 706 has an average flow rate that, during normal operation thereof, is substantially below that of the patient's heart when healthy. The pump 706 may be operated to pump blood from one location in the patient's vasculature to a different location in the vasculature while the proximal end 710 of the first lumen 708 and the proximal end 718 of the second lumen 716 resides outside the patient's body. If desired, the entire system 700 may be implanted into a patient's blood vessel.

If desired, at least one aperture 724 is provided in one of the lumens, in this case lumen 708 and is positioned in the lumen distal from the proximal end 710 so that the aperture(s) 724 may reside within the patient's vasculature, close to the point of insertion. The aperture 724 can maintain or enhance perfusion of blood to the patient's vasculature downstream of where the aperture(s) 724 resides in the vasculature when inserted into the patient. As discussed above, one or more of the lumens of the catheter 704 can have a tapered tip 726. Also, at least one aperture may be positioned proximate a distal end of at least one of the lumens. In other embodiment, a third lumen could be provided that is configured similar to, and functions the same as, the third lumen 134 shown in FIG. 2.

A variety of redirecting tip constructions can be employed in different embodiments of the catheter 704 of the extracardiac pumping system 700, as discussed above; for example redirecting tip 730. Also, the extracardiac pumping system 700 may be provided with a radiopaque marker 728. As discussed above, the marker 728 can be used to position the catheter 704 of the extracardiac pumping system 700 when applied to a patient.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A method of treating a patient comprising:
providing a multilumen catheter, said catheter comprising:
a catheter body having a proximal end, a first distal end, and a second distal end, said first distal end extending distally farther from the proximal end than the second distal end;
a first lumen extending between said first distal end and said proximal end;
a second lumen extending between said second distal end and said proximal end, said second lumen in fluid communication with said first lumen at the proximal end; and
inserting said multilumen catheter into the patient minimally invasively such that the first distal end is at a first vascular location and the second distal end is at a second vascular location remote from the first vascular location;
causing blood to flow in said second lumen to said proximal end and to flow distally from the proximal end in said first lumen without exiting said catheter body; and
redirecting substantially all of the blood flow exiting the first lumen in a direction generally opposite of the direction of flow in the first lumen;
wherein the second vascular location is within a femoral artery or an iliac artery.

2. The method of claim 1, further comprising providing a tip portion having a surface positioned at the distal end of and within the first lumen, the surface configured to redirect substantially all the blood flow exiting the first lumen.

3. The method of claim 2, wherein the surface extends across the first lumen between a side of the first lumen and a central longitudinal axis of the first lumen.

4. The method of claim 2, wherein the surface prevents substantially all of the blood flowing distally in the first lumen from flowing distally beyond the surface.

5. The method of claim 2, wherein the surface comprises a parabolic cross-sectional profile.

6. The method of claim 1, further comprising withdrawing blood at subcardiac rates and causing blood to flow distally in the first lumen at subcardiac rates.

7. The method of claim 1, wherein the first and second vascular locations are both spaced apart from the heart.

8. The method of claim 1, wherein the blood flow exiting the first lumen supplements circulation of the patient.

9. The method of claim 1, wherein redirecting substantially all of the blood flow exiting the first lumen causes the blood exiting the first lumen to flow in substantially the same direction as blood flow at the first vascular location.

10. The method of claim 1, wherein inserting the multilumen catheter into the patient comprises inserting the catheter through a single cannulation site.

11. The method of claim 1, wherein the first lumen has a closed distal end.

12. The method of claim 1, wherein the catheter body has a plurality of side outlets fluidly coupled to the first lumen such that the blood being redirected exits the first lumen through the side outlets.

13. The method of claim 12, where three side outlets are provided in the catheter body.

14. The method of claim 1, further comprising providing a pump within the catheter to direct the flow of blood from the second vascular location to the first vascular location through the catheter.

15. The method of claim 14, further comprising operating the pump at subcardiac rates to cause blood to flow distally in the first lumen to the first vascular location.

16. The method of claim 14, wherein the pump is located within the first lumen of the catheter.

17. The method of claim 14, wherein the pump is located within the second lumen of the catheter.

18. A method of treating a patient comprising:
providing a multilumen catheter, said catheter comprising:
a catheter body having a proximal end, a first distal end, and a second distal end, said first distal end extending distally farther from the proximal end than the second distal end;
a first lumen extending between said first distal end and said proximal end;
a second lumen extending between said second distal end and said proximal end, said second lumen in fluid communication with said first lumen at the proximal end; and
inserting said multilumen catheter into the patient minimally invasively such that the first distal end is at a first vascular location and the second distal end is at a second vascular location remote from the first vascular location;
causing blood to flow in said second lumen to said proximal end and to flow distally from the proximal end in said first lumen without exiting said catheter body; and
redirecting substantially all of the blood flow exiting the first lumen in a direction generally opposite of the direction of flow in the first lumen;
wherein inserting said multilumen catheter into the patient further comprises inserting said catheter into a femoral artery, said first vascular location being the aorta of the patient.

19. The method of claim 18, wherein at least one of the first and second vascular locations is a vascular location in a blood vessel that branches off from a blood vessel directly connected to the heart.

* * * * *

UNITED STATES PATENT AND TRADEMARK OFFICE
CERTIFICATE OF CORRECTION

PATENT NO.       : 7,491,163 B2
APPLICATION NO.  : 11/417647
DATED            : February 17, 2009
INVENTOR(S)      : Anthony Viole et al.

It is certified that error appears in the above-identified patent and that said Letters Patent is hereby corrected as shown below:

Title Pg, Item (56) Other Publications: change "205;" to --2005;--

Title Pg, Item (56) Other Publications, Page 3, Column 2, Line 7, change "Office Office" to --Office, Office--

On Column 7, Line 24-25, change "hemispherially" to --hemispherically--

Signed and Sealed this

Ninth Day of June, 2009

JOHN DOLL
*Acting Director of the United States Patent and Trademark Office*